(12) United States Patent
Weaver et al.

(10) Patent No.: US 6,876,503 B1
(45) Date of Patent: Apr. 5, 2005

(54) MICROSCOPE DRAPE LENS PROTECTIVE COVER ASSEMBLY

(75) Inventors: Richard A. Weaver, Fenton, MI (US); Joseph M. Wright, Fenton, MI (US); Nathan M. Sokolowski, Fenton, MI (US)

(73) Assignee: Contour Fabricators, Inc., Fenton, MI (US)

( * ) Notice: Subject to any disclaimer, the term of this patent is extended or adjusted under 35 U.S.C. 154(b) by 0 days.

(21) Appl. No.: 10/695,634

(22) Filed: Oct. 28, 2003

(51) Int. Cl.[7] .................................................. G02B 7/02
(52) U.S. Cl. .................... 359/818; 359/819; 359/510
(58) Field of Search .............................. 359/811, 818, 359/819, 510; 600/121–5, 112, 174, 131, 133; 128/849–62

(56) References Cited

U.S. PATENT DOCUMENTS

| | | | |
|---|---|---|---|
| 2,285,768 A | 6/1942 | Drucker ...................... 359/819 |
| 2,431,825 A | 12/1947 | Pollock ...................... 396/425 |
| 3,410,635 A | 11/1968 | Lockwood .................. 359/804 |
| 3,528,720 A | 9/1970 | Treace ........................ 359/510 |
| 3,542,450 A | 11/1970 | Terhune ...................... 359/510 |
| 3,698,791 A | 10/1972 | Walchle ...................... 359/510 |
| 3,713,725 A | 1/1973 | Uesugi ........................ 359/813 |
| 3,796,477 A | 3/1974 | Geraci ........................ 359/511 |
| 4,045,118 A | 8/1977 | Geraci ........................ 359/510 |
| 4,088,396 A | 5/1978 | Edelstein .................... 359/822 |
| 4,183,613 A | 1/1980 | Walchle et al. ............. 359/510 |
| 4,266,663 A | 5/1981 | Geraci ........................ 359/510 |
| 4,561,540 A | 12/1985 | Hunter et al. ............... 209/305 |
| 4,564,270 A | 1/1986 | Willie ........................ 359/511 |
| 4,799,779 A | 1/1989 | Mesmer ...................... 359/510 |
| 5,155,624 A | 10/1992 | Flagler ....................... 359/510 |
| 5,274,500 A | 12/1993 | Dunn .......................... 359/507 |
| 5,311,358 A | 5/1994 | Pederson et al. ........... 359/510 |
| 5,467,223 A * | 11/1995 | Cleveland et al. .......... 359/510 |
| 5,608,574 A | 3/1997 | Heinrich ..................... 359/510 |
| 5,682,264 A | 10/1997 | Cleveland et al. .......... 359/510 |
| 5,696,635 A | 12/1997 | Kastner ....................... 359/872 |
| 5,853,363 A | 12/1998 | Vought ....................... 600/121 |
| 5,959,789 A | 9/1999 | Rando ......................... 359/822 |
| 6,024,454 A | 2/2000 | Horan et al. ................ 359/810 |
| 6,056,409 A * | 5/2000 | Grinblat ...................... 359/503 |
| 6,116,741 A | 9/2000 | Paschal ....................... 359/510 |
| 6,198,580 B1 | 3/2001 | Dallakian .................... 359/822 |
| 6,257,730 B1 | 7/2001 | Kleinberg et al. .......... 359/600 |
| 6,318,864 B1 | 11/2001 | Fukaya et al. .............. 359/510 |
| 6,560,045 B1 | 5/2003 | Schletterer .................. 359/819 |
| 6,562,026 B2 * | 5/2003 | Glockler ...................... 606/10 |
| 2001/0036023 A1 | 11/2001 | Dallakian .................... 359/822 |
| 2001/0038499 A1 | 11/2001 | Baartman et al. ........... 359/821 |

* cited by examiner

*Primary Examiner*—Jordan M. Schwartz
*Assistant Examiner*—Jessica Stultz
(74) *Attorney, Agent, or Firm*—John K. McCulloch

(57) ABSTRACT

A protective cover for removable attachment to an objective lens housing of a draped surgical microscope has a primary, annular retainer of such size as to encircle and engage the lens housing. The retainer has an external frusto-spherical surface and an internal surface capable of seating on and snugly engaging the lens housing. The retainer removably supports a transparent shield for protecting the lenses in the lens housing. A secondary annular retainer encircles the primary retainer and has an internal surface which seats on and is supported by the external surface of the primary retainer. The secondary retainer removably accommodates a second transparent shield forming a closure for the secondary retainer. The second retainer is axially, rotatably, and rockably adjustable relative to the primary retainer for minimizing the transmission of glare to the microscope.

27 Claims, 3 Drawing Sheets

MICROSCOPE DRAPE LENS PROTECTIVE COVER ASSEMBLY

This invention relates to a surgical microscope lens protective cover assembly of the kind used in conjunction with sterile drapes which maintain a sterile field above a patient during the performance of an invasive surgical procedure.

BACKGROUND OF THE INVENTION

The use of a surgical microscope by a surgeon during an invasive surgical procedure is common. The surgical microscope conventionally includes an objective lens housing or barrel typically enclosed within a sterile drape constituted by a thin, plastic film. The drape conventionally has an opening therein through which the objective lens housing of the microscope projects so that the drape film does not interfere with the ability of the surgeon to maintain clear visibility of the surgical site. The opening through which the objective lens housing extends conventionally is provided with a seal so as to avoid the provision of a path adjacent the opening through which contamination may pass. Some of the known constructions have elastic fittings which grip the objective lens housing and support transparent window-like panes through which light may pass from the microscope to illuminate the surgical field.

The use of conventional microscope lens protective cover assemblies has presented two distinct problems: first, the transparent window-like pane may become contaminated by spurting biological fluids. Cleaning or replacement of the pane is both difficult and time consuming, particularly when the cleaning or replacement must be accomplished by gloved-hand personnel.

The second difficulty attributable to surgical microscope lens cover assemblies is the presence of undesirable transient light or glare caused by reflection or refraction of light in such manner as to interfere with the surgeon's view of the surgical site.

A principal object of the invention is to overcome the difficulties noted above with respect to heretofore available protective lens cover assemblies.

SUMMARY OF THE INVENTION

Apparatus constructed in accordance with the invention is adapted for use in conjunction with a surgical microscope of the kind having eyepieces through which one or more persons, such as a surgeon and assistants, may view a surgical site. A typical surgical microscope is mounted on a support which enables the microscope to be positioned at a level above or to one side of a patient, the microscope having an objective lens assembly mounted within a housing or barrel which may be positioned a selected distance from the site. Conventionally, the microscope includes a source of light which passes through the objective lens housing for illuminating the surgical site. Since the microscope quite often is positioned very close to the surgical site it is not uncommon for surgical procedures to cause body fluids to traverse the distance between the patient and the objective lens and contaminate and/or smear the latter. Contamination of the lens interferes with the surgeon's view of the surgical site.

Because of the proximity of the microscope to the surgical site on some occasions it is customary to enclose the microscope within a sterile drape. It also is conventional to provide a protective cover or shield for the outermost objective lens of the microscope, the shield being removable for replacement in the event it becomes contaminated or smeared by contact with body fluids. The cleaning or replacement of a contaminated lens shield or cover frequently is hampered by the necessity of the person charged with cleaning or replacement to be gloved.

Another frequently encountered problem when using surgical microscopes is that the optical path from the surgical site to the eyepieces may be distorted, obscured, or blurred by the reflection or refraction of light either from the illuminating source or from other lighting in the area where the surgery is being conducted. Sometimes the lens cover or shield when in its best position for optical acuity is subjected to glare which cannot be removed if the lens is to remain in its optimum position. Apparatus constructed in accordance with the invention provides an additional or secondary holder for a shield or cover which can be applied to the objective lens barrel in such manner as to enable the shield to be both rocked and rotated to any selected one of a number of adjusted positions in which the visual acuity is optimum. The construction of the apparatus according to the invention is such as to facilitate not only the attachment of the additional shield holder to the lens barrel but also enable extremely rapid and facile adjustment of the holder and the shield carried thereby, while ensuring snug retention of the holder in its selected position of adjustment.

THE DRAWINGS

The foregoing characteristics of the invention are disclosed in the following description and illustrated in the accompanying drawings wherein.

THE PREFERRED EMBODIMENT

Figure 1:
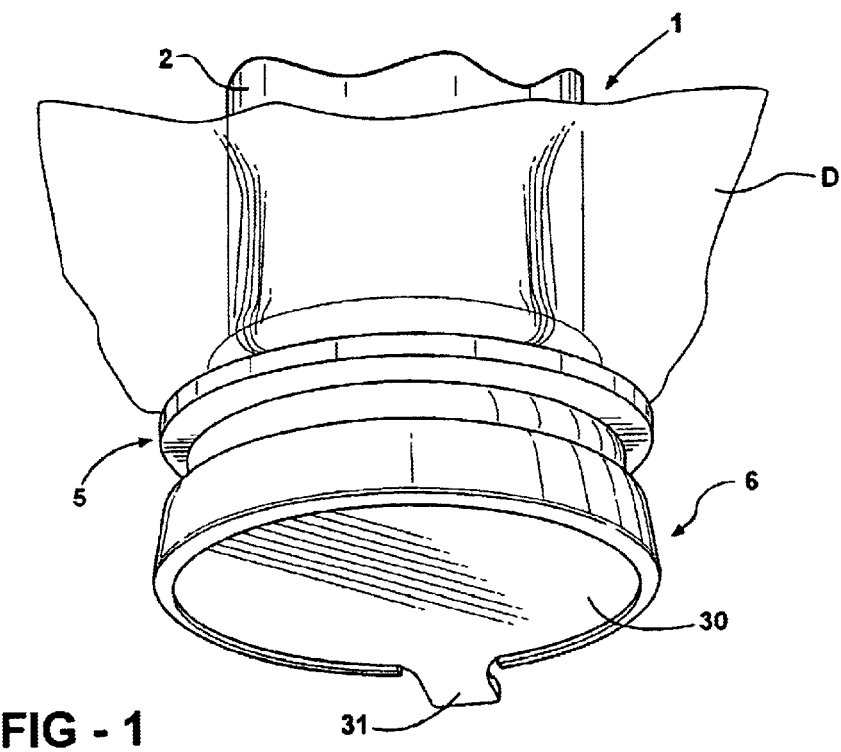
FIG. 1 is a fragmentary, isometric view illustrating the lower end of a surgical microscope's objective lens barrel, a portion of a sterile drape, and a two-part, separable assembly for the removable support of a protective shield.

Apparatus constructed in accordance with the preferred embodiment of the invention is especially adapted for use with a surgical microscope of known construction having an objective lens housing or barrel 1 which extends beyond the microscope housing and contains objective lenses (not shown) through which light may pass from a source (not shown) of illumination through the housing to the surgical site, and thence, to the eyepiece or eyepieces (not shown) through which a surgeon and/or assistants may view the site. The housing 1 typically has a cylindrical wall 2 having a free end 3 encircled by circumferentially spaced, longitudinally extending ribs 4 which project radially outwardly. The apparatus described thus far is conventional and forms no part of the invention except for the manner in which it cooperates with apparatus yet to be described.

The preferred embodiment of the invention comprises a first annular retainer 5 and a second annular retainer 6. The first retainer may be used independently of the second retainer 6 or in conjunction with the latter as will be explained hereinafter.

The first retainer 5 has a annular wall 7 terminating at one end in a radially directed flange 8 having a smooth, flat or planar surface 9. The opposite end of the wall 7 terminates in a flat or planar surface 10. The external surface 11 of the wall 7 is frusto-spherical for a purpose subsequently to be explained.

The inner surface of the wall 7 forms a cylindrical bore 12 joined at its upper end to a radially inwardly extending projection 13 terminating at its upper end in a tapered mouth 14. Adjacent its lower end the surface of the bore 12 is joined to an inwardly projecting, continuous, annular, upper rib 15 which is axially spaced from a second or lower inwardly projecting rib 16. The ribs 15 and 16 are axially spaced apart so as to form between them a continuous groove 17.

The wall 7 is provided with a notch 18 at a selected zone and such slot also extends through the corresponding zone of the lowermost rib 16. However, the upper rib 15 is continuous.

Adapted for removable accommodation in the annular groove 17 formed by the ribs 15 and 16 is a transparent cover or shield 19 formed of glass or suitable plastic material, as is conventional. The shield 19 is cylindrical except for a tab 20 which extends radially and is provided with a reinforcement 21 which is adhesively or otherwise suitably secured to the tab 20. The tab and reinforcement extend through the notch 18 when the shield 19 is accommodated in the annular groove 17.

The apparatus thus far described is adapted to be used in conjunction with a sterile drape D comprising a sheet of thin, pliable, transparent material, such as a copolymer capable of being heat sealed to the surface of the flange 8 at the upper end of the first retainer 5. The drape is provided with an opening 0 for the accommodation of the lower portion of the objective lens barrel 1 of the surgical microscope.

When the drape D is secured to the flange 8 the drape and the first retainer 5 form an integral, unitary construction which may be assembled with the surgical microscope. To perform the assembly the drape D is so oriented to the barrel 1 that the mouth 14 of the retainer 5 underlies the free end of the objective barrel 1 so that the retainer 5 may be applied in encircling relation to the lower end of the barrel. Assembly is facilitated by the tapered mouth of the retainer. The material from which the retainer 5 is made preferably is elastomeric and has sufficient elasticity to enable it to grip the projections 4 and snugly, but removably, maintain the retainer on the barrel. A suitable material is that manufactured and sold by Shell Oil Company under the trademark KRATON.

The transparent shield 19 may be fitted into the annular groove 17 of the retainer 5 either before or after the latter is fitted to the lower edge of the barrel 1. It will be understood that the drape D is of such size as to envelope a surgical microscope and maintain a sterile environment above the surgical site.

Following assembly of the retainer and shield 19 with the lens barrel 1, the shield provides a protective cover for the lenses in the barrel so as to shield them from contamination by body fluids or other sources during the performance of the surgical procedure. Should one shield 19 be subjected to smearing from an attendant's gloved hand or some other source, such shield may be removed from the retainer and replaced by another. The tab 20 and the notch 18 facilitate the removal and replacement of shields.

Although the lower rib 16 which assists in forming the annular groove 17 is discontinuous at the zone of the notch 18, the upper rib 15 is continuous, thereby ensuring an effective contamination barrier at the juncture of the retainer 5 and the lens barrel 1.

There are instances when circumstances are such that the view through the microscope of the surgical site is somewhat impaired by glare produced by reflection or refraction of the site-illuminating light generated by the microscope or by the reflection or refraction of ambient light from other sources. In these instances the glare can be eliminated or greatly minimized by the use of the second retainer 6.

The retainer 6 comprises a frusto-conical wall 22 having an outer surface 23 and a smooth inner surface 24 forming a tapered bore. The diameter of the bore at its upper, smaller diameter end is slightly less than that of the outer surface 11 of the wall 7 at its maximum diameter, whereas the diameter of the larger end of the bore 24 is greater than that of the outer surface 11 of the wall 7 at its maximum diameter. The material from which the retainer 6 is made may be the elastic polymer, KRATON, thereby enabling the smaller diameter end of the wall 22 to be flexed outwardly a distance sufficient to permit the retainer 6 to be mounted on and supported by the retainer 5.

Adjacent the larger diameter end of the wall 22 is an endless groove 25 having a continuous upper edge 26 and a tapered lower edge 27 formed by a lip 28. Both the wall 22 and the lip 28 are discontinuous at corresponding zones to provide a notch 29.

A transparent shield or cover 30 like the shield 19 has a laterally projecting tab 31 provided with a reinforcement 32 so as to facilitate movement of the shield 30 into and out of the groove 25.

When use of the second retainer 6 is deemed desirable it may be fitted onto the retainer 5 simply by placing its smaller diameter and in register with the retainer 5 and moving it axially upwardly to the position in which the smaller diameter end of the bore 24 has passed the maximum diameter of the surface 11 of the wall 7. See FIGS. 2 and 3. The inner surface of the bore of the retainer wall 6 then will engage the wall 7 and the retainer 6 will be suspended from the retainer 5.

Although the shield 19 may remain in assembled relation with the retainer 5, it is contemplated that, when the retainer 6 and its associated shield 30 are used, the shield 19 will be removed from the retainer 5.

Figure 2:
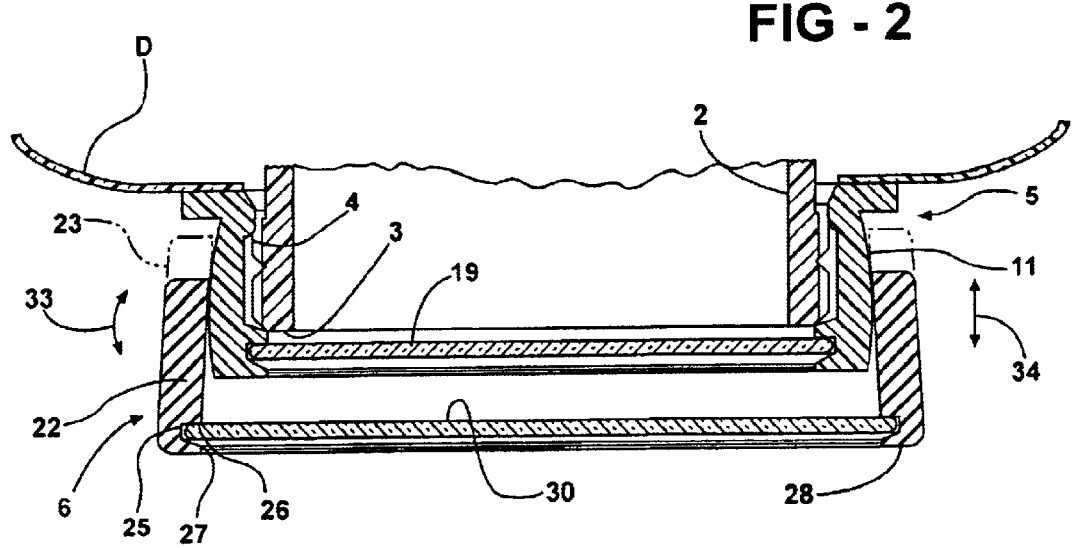
FIG. 2 is an enlarged, transverse sectional view of a portion of the apparatus shown in FIG. 1.
Figure 4:
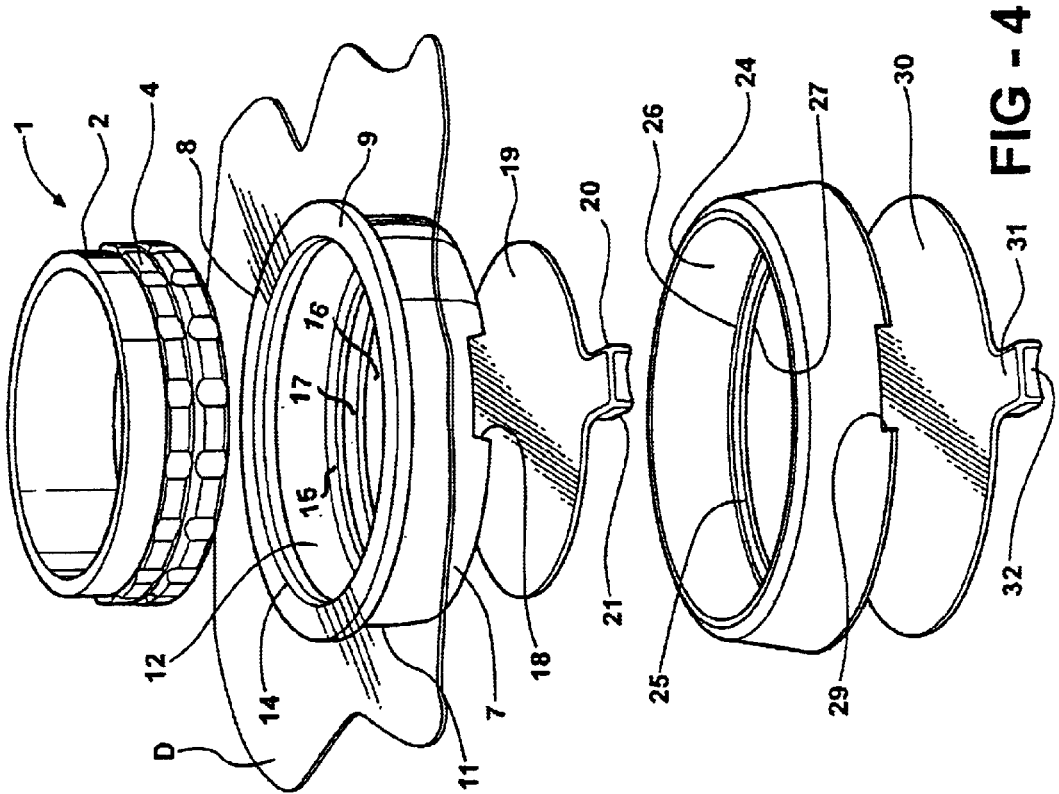
FIG. 4 is an exploded, isometric view of the components of the apparatus.
Figure 3:
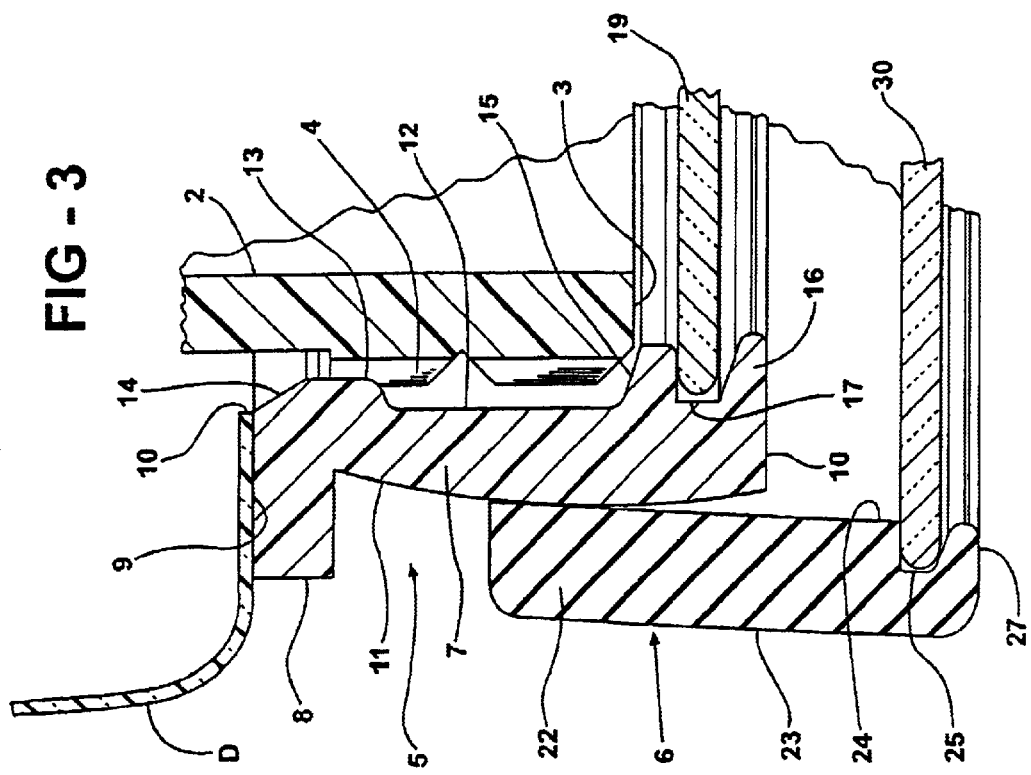
FIG. 3 is a fragmentary, greatly enlarged view of a portion of the apparatus shown in FIG. 2.
Figure 5:
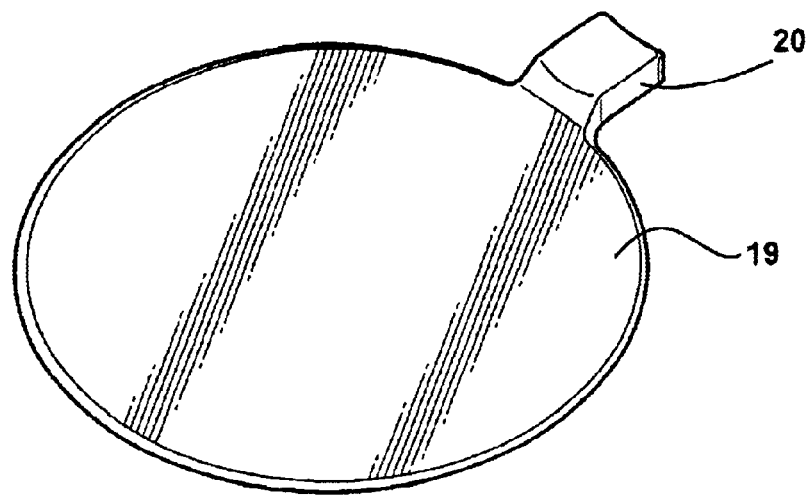
FIG. 5 is an isometric view, on an enlarged scale, of a shield forming part of the apparatus.
Figure 6:
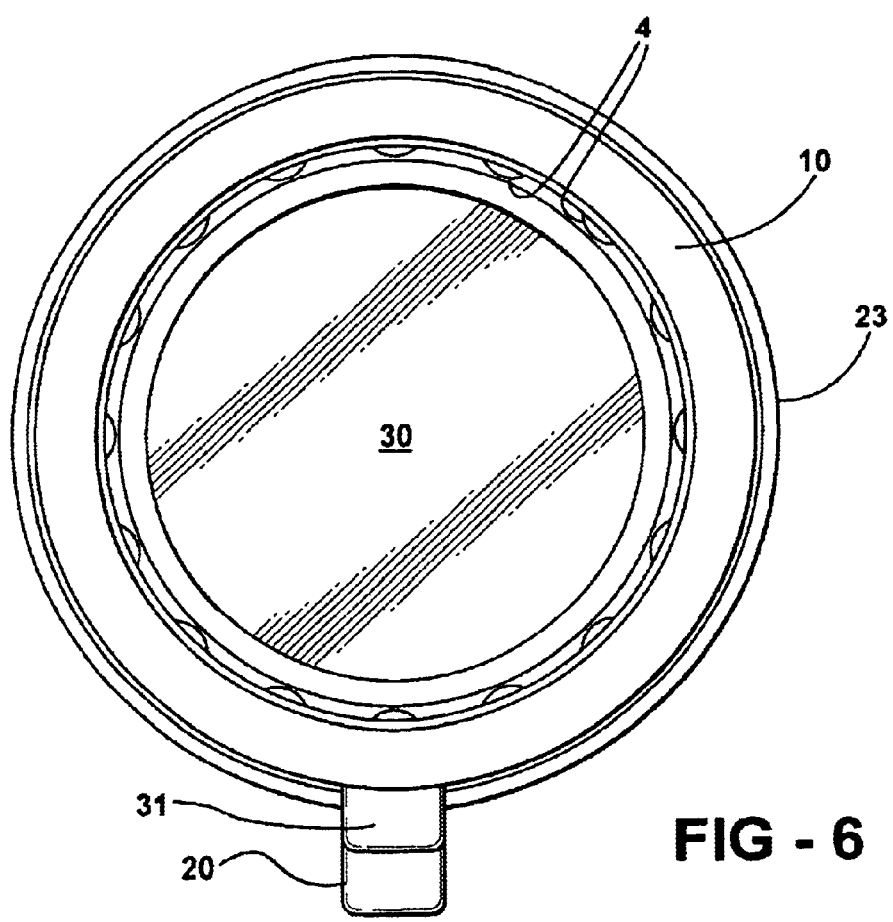
FIG. 6 is a bottom plan view of the assembled apparatus shown in FIG. 4.

Once the retainer 6 is assembled on the retainer 5, the retainer 6 may be rocked about an arc having a radius corresponding to that of the arcuate surface 11 of the wall 7, as is indicated by the double arrow 33 in FIG. 2. The retainer 6 also may be rotated relative to the retainer 5. To facilitate such rocking and rotation, the retainer 6 may be adjusted axially, as indicated by the double arrow 34 in FIG. 2, so as to disengage the surfaces 7 and 24, thereby minimizing or eliminating the frictional force between the retainers 5 and 6. Once the retainer 6 has been rotated or rocked to the desired position, it may be moved downwardly so as once again to effect snug engagement between the engaged walls of the retainers and maintain the retainer 6 in any selected one of a number of adjusted positions relative to the retainer 5. The engagement between the confronting walls of the retainers 5 and 6 will ensure contact therebetween sufficient to block the passage of contaminants.

If the shield 19 is maintained within the retainer 5 when the retainer 6 is mounted on the retainer 5, the shield 19 cannot be removed from the retainer 5 without first removing the retainer 6. However, in this circumstance the shield 19 will be protected by the shield 30. The shield 30, of course, can be removed from the retainer 6 any time and replaced by another.

The disclosed embodiment is representative of a presently preferred form of the invention, but is intended to be illustrative rather than definitive thereof. The invention is defined in the claims.

We claim:

1. Apparatus for use with a drape capable of enclosing a surgical microscope having a lens housing, said apparatus comprising a first retainer of such size as to encircle and separably grip said lens housing; a second retainer encircling said first retainer, said second retainer being adjustable relative to said first retainer and being so configured as releasably to remain in any selected one of a number of positions of adjustment relative to said first retainer; and means carried by at least one of said retainers for supporting a transparent shield in a position to protect lenses in said lens housing from contamination.

2. Apparatus according to claim 1 wherein each of said retainers is annular.

3. Apparatus according to claim 1 wherein said second retainer is reciprocable relative to said first retainer.

4. Apparatus according to claim 1 wherein said second retainer is rockable relative to said first retainer.

5. Apparatus according to claim 1 wherein said second retainer is rotatable relative to said first retainer.

6. Apparatus according to claim 1 wherein said second retainer is axially reciprocable, rockable, and rotatable relative to said first retainer.

7. Apparatus according to claim 1 wherein said one of said retainers has a frusto-spherical wall and the other of said retainers has a wall encircling said frusto-spherical wall.

8. Apparatus according to claim 7 wherein said wall of said other of said retainers is linear.

9. Apparatus according to claim 8 wherein said wall of said other of said retainers tapers in one direction.

10. Apparatus according to claim 1 wherein said shield has a tab extending outwardly therefrom.

11. Apparatus according to claim 1 wherein the means for supporting said transparent shield comprises an annular groove in the wall of said one of said retainers and in which said shield is accommodated.

12. Apparatus according to claim 11 wherein said groove is formed by first and second annular ribs parallel to and spaced from one another.

13. A protective cover construction for removable attachment to an objective lens housing of a surgical microscope, said construction comprising a primary retainer of such size as to encircle and engage said lens housing, said retainer having an external frusto-spherical surface and an internal surface adapted to seat on and snugly engage said lens housing; support means at said internal surface for supporting a transparent shield which forms a closure for said retainer; a secondary retainer of such size as to encircle said primary retainer and having an internal surface operable to seat on and be supported by the external surface of said primary retainer; and means adjacent one end of said internal surface of said secondary retainer for accommodating and retaining a second transparent shield operable to form a closure for said secondary retainer, said secondary retainer being adjustable relative to said primary retainer to any selected one of a number of positions of adjustment, the engagement of the external and internal surfaces of said primary and secondary retainers respectively being operable to maintain said retainers in said selected position of adjustment.

14. The construction according to claim 13 wherein said internal surface of said secondary retainer is tapered in a direction from said one end of said internal surface toward its opposite end.

15. The construction according to claim 14 wherein the internal surface of said secondary retainer at said one end thereof has a diameter greater than that of said opposite end thereof, the diameter of the opposite end of said internal surface of said secondary retainer being less than the maximum diameter of said frusto-spherical surface of said primary retainer.

16. The construction according to claim 15 wherein said internal surface of said secondary retainer has a height sufficient to enable axial movement of said secondary retainer relative to said primary retainer a distance sufficient to reduce the force with which the internal surface of said secondary retainer engages the external surface of said primary retainer.

17. The construction according to claim 13 wherein said primary retainer is formed of elastomeric material.

18. The construction according to claim 11 wherein said secondary retainer is formed of elastomeric material.

19. The construction according to claim 13 wherein said internal surface of said primary retainer has at least one annular enlargement projecting radially inwardly for circumferential engagement with said lens housing.

20. A protective cover construction for a surgical microscope having an objective lens housing, said construction comprising a first retainer having an annular wall of such size as to encircle and snugly engage said lens housing, said annular wall having an external frusto-spherical surface; a second retainer having an annular wall whose inner surface is of such diameter as to encircle said one end of said first retainer and snugly engage said external surface thereof whereby said first retainer provides support for said second retainer; and retaining means carried by said second retainer adjacent one end thereof for accommodating and supporting a transparent shield forming a closure for said second retainer, said second retainer being movable relative to said first retainer to any selected one of a plurality of adjusted positions, the engagement between said respective external and internal surfaces exerting sufficient force to maintain said second retainer in said selected one of said positions.

21. The construction according to claim 20 wherein said first retainer has support means for supporting a second transparent shield which forms a closure for said second retainer.

22. The construction according to claim 20 wherein the internal surface of said wall of said second retainer has a diameter which diminishes in a direction from said one end thereof toward its opposite end.

23. The construction according to claim 22 wherein said internal surface of said second retainer has a maximum diameter adjacent said one end of said wall greater than the maximum diameter of said frusto-spherical surface of said first retainer and a minimum diameter adjacent said opposite end less that the maximum diameter of said frusto-spherical surface of said first retainer.

24. The construction according to claim 20 wherein said wall of said second retainer has a height sufficient to enable movement of said second retainer axially relative to said first retainer a distance sufficient to reduce the force exerted on said first retainer by said second retainer.

25. The construction according to claim 24 wherein said wall of said second retainer has a height sufficient to enable axial movement of said retainer member relative to said first retainer a distance sufficient to effect disengagement between the respective external and internal surfaces of said first and second retainers.

26. The construction according to claim 1 wherein said first retainer has an annular, radially extending flange adjacent its opposite end for attachment to a drape.

27. The construction according to claim 26 including a drape having therein an opening of such size as to accommodate said objective lens housing, said opening being coaxial with said first retainer, the material of such drape adjacent said opening being adhered to said flange.

* * * * *